United States Patent [19]
Tsukernik et al.

[11] Patent Number: 5,643,318
[45] Date of Patent: Jul. 1, 1997

[54] VASCULAR PLUG WITH VESSEL LOCATOR

[75] Inventors: Vladimir B. Tsukernik, Brookline; William J. Shaw, Cambridge, both of Mass.

[73] Assignee: Boston Scientific Corporation, Watertown, Mass.

[21] Appl. No.: 684,333

[22] Filed: Jul. 19, 1996

Related U.S. Application Data

[63] Continuation of Ser. No. 221,355, Mar. 31, 1994, abandoned.

[51] Int. Cl.⁶ .................................................. A61B 17/04
[52] U.S. Cl. ............................ 606/214; 606/216; 604/15
[58] Field of Search .......................... 128/DIG. 8; 604/13, 604/15, 51, 60, 158; 606/213–215, 216, 228–232; 623/1, 12, 15

[56] References Cited

U.S. PATENT DOCUMENTS

| | | | |
|---|---|---|---|
| 3,196,873 | 7/1965 | Bletzinger et al. | 604/15 |
| 4,390,018 | 6/1983 | Zukowski | 128/303 R |
| 4,744,364 | 5/1988 | Kensey | 128/334 R |
| 4,774,091 | 9/1988 | Yamahira et al. | 424/426 |
| 4,790,819 | 12/1988 | Li et al. | 604/59 |
| 4,838,280 | 6/1989 | Haaga | 128/751 |
| 4,852,568 | 8/1989 | Kensey | 128/325 |
| 4,890,612 | 1/1990 | Kensey | 606/213 |
| 4,929,246 | 5/1990 | Sinofsky | 606/8 |
| 4,936,835 | 6/1990 | Haaga | 604/265 |
| 5,021,059 | 6/1991 | Kensey et al. | 606/213 |
| 5,053,046 | 10/1991 | Janese | 606/215 |
| 5,061,274 | 10/1991 | Kensey | 606/213 |
| 5,080,655 | 1/1992 | Haaga | 604/265 |
| 5,108,421 | 4/1992 | Fowler | 606/213 |
| 5,192,300 | 3/1993 | Fowler | 606/213 |
| 5,192,302 | 3/1993 | Kensey et al. | 606/213 |
| 5,195,988 | 3/1993 | Haaga | 604/265 |
| 5,221,259 | 6/1993 | Weldon et al. | 604/96 |
| 5,222,974 | 6/1993 | Kensey et al. | 606/213 |
| 5,254,105 | 10/1993 | Haaga | 604/265 |
| 5,275,616 | 1/1994 | Fowler | 606/213 |
| 5,282,827 | 2/1994 | Kensey et al. | 606/215 |
| 5,290,310 | 3/1994 | Makower et al. | 606/213 |
| 5,292,309 | 3/1994 | Van Tassel et al. | 604/117 |
| 5,292,332 | 3/1994 | Lee | 606/213 |
| 5,306,254 | 4/1994 | Nash et al. | 604/168 |
| 5,310,407 | 5/1994 | Casale | 604/51 |
| 5,312,435 | 5/1994 | Nash et al. | 606/213 |
| 5,320,639 | 6/1994 | Rudnick | 606/213 |
| 5,334,216 | 8/1994 | Vidal et al. | 606/213 |
| 5,370,660 | 12/1994 | Weinstein et al. | 606/215 |
| 5,411,520 | 5/1995 | Nash et al. | 606/213 |
| 5,415,657 | 5/1995 | Taymor-Luria | 606/49 |
| 5,431,639 | 7/1995 | Shaw | 604/264 |
| 5,437,292 | 8/1995 | Kipshidze et al. | 128/898 |
| 5,437,631 | 8/1995 | Janzen | 604/49 |

FOREIGN PATENT DOCUMENTS

| | | |
|---|---|---|
| 0 139 091 A1 | 5/1985 | European Pat. Off. . |
| 0 476 178 A1 | 3/1992 | European Pat. Off. . |
| 0 482 350 A2 | 4/1992 | European Pat. Off. . |
| WO 90/14796 | 12/1990 | WIPO . |
| WO 92/05740 | 4/1992 | WIPO . |
| WO 92/22252 | 12/1992 | WIPO . |
| WO 93/07813 | 4/1993 | WIPO . |
| WO 93/08746 | 5/1993 | WIPO . |
| WO 94/02072 | 2/1994 | WIPO . |

OTHER PUBLICATIONS

Rosen, "Diagnostic Angiography", 1986.
Takayasu et al., "A New Hemostatic Procedure for Percutaneous Transhepatic Portal Vein Catheterization," *Jpn. J. Clin. Oncol.*, 18, pp. 227–230, 1988.

*Primary Examiner*—Robert A. Clarke
*Attorney, Agent, or Firm*—Fish & Richardson P.C.

[57] ABSTRACT

The invention relates to a hemostatic plug having its own vessel wall locating system. The hemostatic plug allows accurate positioning of itself within an access incision, e.g., to a blood vessel, so that it is adjacent to, but does not extend beyond the vessel wall into the vessel lumen.

24 Claims, 15 Drawing Sheets

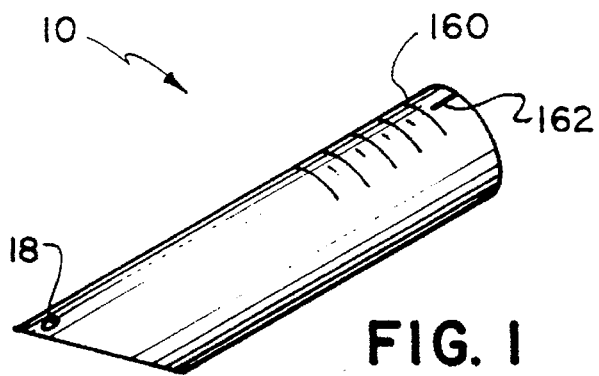
FIG. 1
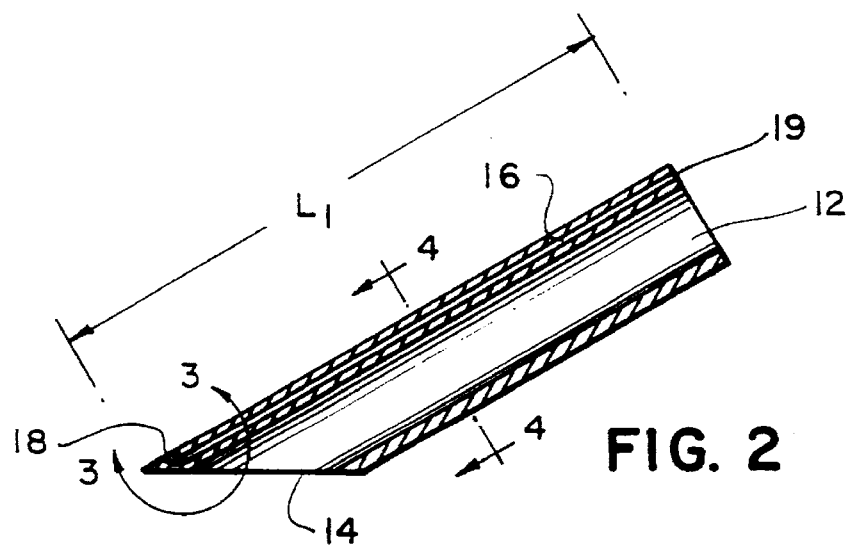
FIG. 2
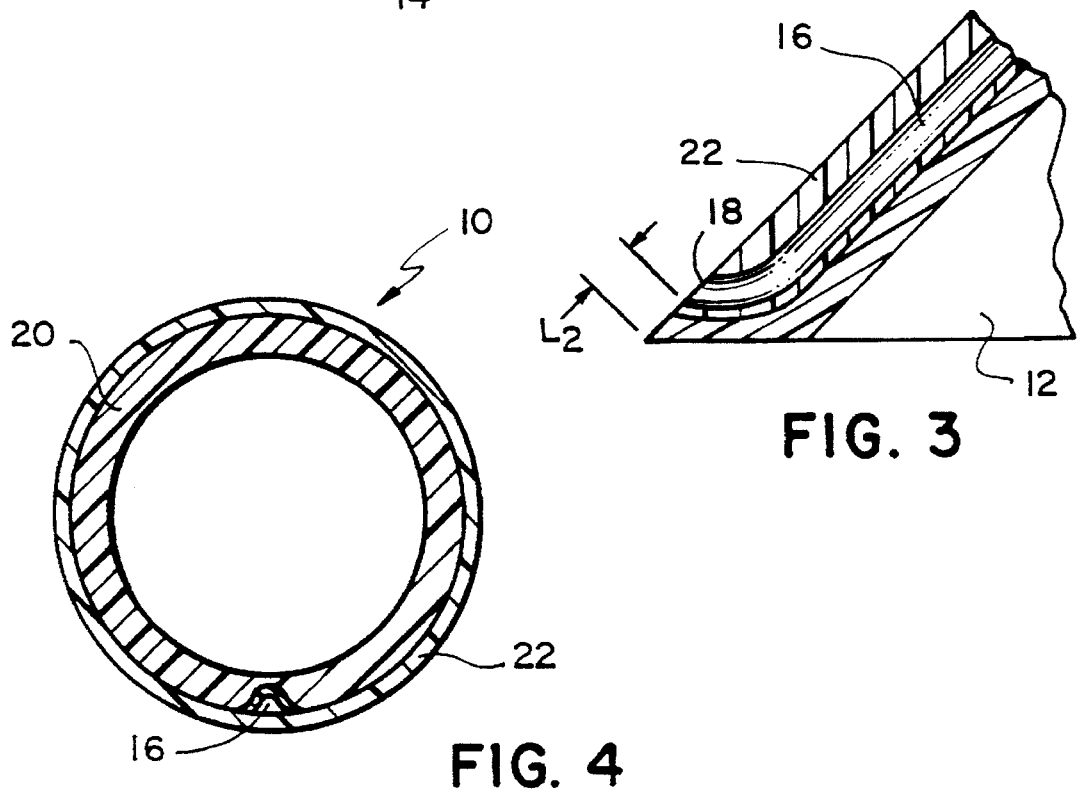
FIG. 3
FIG. 4

VASCULAR PLUG WITH VESSEL LOCATOR

This is a continuation of application Ser. No. 08/221,355, filed Mar. 31, 1994, now abandoned.

FIELD OF THE INVENTION

This invention relates to treating wounds caused by medical procedures.

BACKGROUND OF THE INVENTION

In many medical procedures, a medical device must be placed in tissue that is well below the exposed surface of the body. Typically, an incision or puncture is made through surrounding tissue to gain access to the target tissue. After the procedure, the access incision is usually treated to encourage healing.

For example, in balloon angioplasty procedures, a narrow access channel is cut that extends from the body surface through the skin, the subcutaneous fascia (e.g. connective tissue, fat and muscle), and the wall of a blood vessel. An access catheter is placed in the access channel and the angioplasty catheter delivered into the vessel through the access catheter. At the end of the procedure, the access catheter is removed from the body. The access channel is treated to prevent excessive bleeding by applying manual pressure to the site or depositing a hemostatic material into the channel.

SUMMARY OF THE INVENTION

The invention relates to a hemostatic plug having its own vessel wall locating system that allows the plug to be accurately positioned within an access incision, e.g., to a blood vessel, so that its distal end is adjacent to, but does not extend beyond the vessel wall into the vessel lumen.

In one aspect of the invention, a plug for treating an incision channel through tissue and the wall of a body lumen, includes a sealing member formed of a healing promoting substance having an elongate generally tubular shape and constructed to be introduced axially into the incision and be moveable axially therein. The member includes portions constructed to define an integral flow path extending from a distal end of the sealing member to a proximal end of the sealing member. The flow path is accessed from the side of member such that body fluid flows along the flow path to the proximal portion of the plug when a portion of the plug including the flow path is exposed to the interior of the body lumen.

Embodiments may include one or more of the following features. The sealing member is primarily formed of a first healing promoting substance that rapidly expands upon exposure to body fluid and includes a second healing-promoting substance that expands less rapidly than the first healing-promoting substance with the second healing-promoting substance being provided on the portions of the member defining the flow path. The second healing-promoting substance may be in the form of a thin coating over the first healing-promoting substance and may substantially coat the outer exposed portions of the member. The flow path is formed by a lumen that is accessed through an access opening near the distal end of the plug. The walls of the lumen are formed of the second healing-promoting substance. The member includes a flow channel along its side, such that, when the member is in the incision channel the flow path is between the flow channel and the tissue on the wall of the incision adjacent the flow channel. The flow channel has an oblong cross section with depth being greater than the width, for example, the depth of the flow channel is at least about one fourth of the overall diameter of the generally tubular member. The plug includes a removable support lumen disposed within the integral flow path during positioning of the plug and slidably removed after positioning. The removable support lumen is a non-biodegradable substance. A distal end of the sealing member includes an outer coating of a non-hemostatic material. The sealing member includes a series of marks with known axial distance relationships to the most distal portion of flow path that is accessed from the side of the member. The sealing member includes a delivery lumen sized and constructed to allow delivery of the plug into the incision over a catheter and to allow sliding delivery of the member over an introducer catheter.

In another aspect of the invention, a system for treating an incision through tissue and the wall of a body lumen, includes a catheter having a proximal portion constructed to remain outside the body and an elongate generally tubular distal portion that is constructed to be introduced axially into the incision and a sealing member formed of a healing promoting substance having an elongate generally tubular shape and constructed to be introduced axially into the incision. The member includes portions constructed to define an integral flow path extending from a distal end of the sealing member to a proximal end of the sealing member with the flow path being accessed from the side of member such that body fluid flows along the flow path to the proximal portion of the plug when a portion of the plug including the flow path is exposed to the interior of the body lumen. The sealing member is constructed and dimensioned to be guided into the incision by the catheter.

In embodiments of the invention, the catheter includes an inner lumen adapted for introducing a medical device to the body lumen. The sealing member is slidably disposed on the catheter and is constructed to be introduced into the incision simultaneously with the guide member and released from the guide member by sliding the guide member proximally relative to the sealing member.

In another aspect of the invention, a method of positioning a sealing member within an incision through tissue and the wall of a body lumen includes providing a sealing member formed of a healing promoting substance having an elongate generally tubular shape and constructed to be introduced axially into the incision and be moveable axially therein. The member includes portions constructed to define an integral flow path extending from a distal end of the sealing member to a proximal end of the sealing member, with the flow path being accessed from the side of member such that body fluid flows into the flow path to the proximal portion of the plug when a portion of the plug including the flow path is exposed to the interior of the body lumen. The method includes the steps of introducing the sealing member within the incision until the access opening is exposed to the interior of the body lumen so that a flow of body fluid is provided to the integral flow path and moving the sealing member in an axial direction until the flow of body fluid provided to the integral flow path ceases.

In embodiments of the invention, the method may include one or more of the following steps. The introducing step includes providing the sealing member over a catheter. The catheter is introduced into the incision prior to introducing the sealing member. The catheter and sealing member are introduced into the incision simultaneously.

Further aspects, features and advantages follow.

BRIEF DESCRIPTION OF THE DRAWING

FIG. 1 is a perspective view of a plug for treating an access channel;

FIG. 2 is a cross-sectional side view of the plug of FIG. 1;

FIG. 3 is an enlarged view of the distal tip end of the plug within line 3—3 in FIG. 2;

FIG. 4 is an enlarged end-on cross-sectional view along lines 4—4 in FIG. 2;

FIG. 10 shows the plug and access catheter prior to insertion within the incision channel;

FIG. 12 shows the plug and access catheter prior to insertion within the incision channel;

DESCRIPTION OF THE PREFERRED EMBODIMENTS

Figure 5:
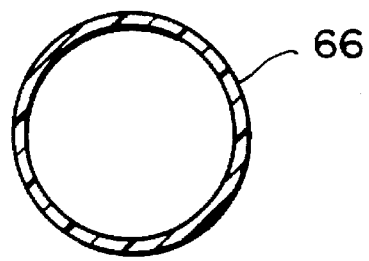
FIG. 5 shows the outer shell of the plug.

Referring to FIGS. 1–4, a vascular plug 10 for treating an access channel to the femoral artery after a catheterization (e.g. angioplasty) or similar procedure is shown. Vascular plug 10 includes an internal lumen 12, which extends from the proximal end of the plug to a distal end opening 14, allowing delivery of the plug over a directing device such as a conventional introducer catheter of the type used to deliver angioplasty catheters or the like to the lumen.

Vascular plug 10 includes its own vessel wall locating system in the form of a lumen 16 that defines a flow path extending from an opening 18 near the distal end to an opening 19 at the proximal end of the plug. As the plug is slid in the access channel, the flow of blood through the lumen, or lack thereof, is observed to locate the plug at an axial depth near the vessel, but so as not to extend beyond the vessel wall into the vessel lumen.

Lumen 16 has an oblong or U-shaped cross section (about 1.75 mm$^2$) with its long dimension (1 to 2 mm) being typically about one-fourth the diameter of plug 10. The oblong cross section ensures that a clear, unobstructed flow path is provided after insertion into the access channel which tends to flatten out the flow channel due to the surrounding pressure from the tight fit of the plug. Access opening 18 is positioned, $L_2$, about 0.1 to 0.25 mm, from the distal face of plug 10 and is formed as a notch-cut through the exterior of plug 10.

Vascular plug 10 is fabricated from biodegradable materials so that it need not be removed surgically after the access channel has healed. The inner layer 20 of soft bovine collagen (about 0.5 to 1.0 mm thick) is of a type which rapidly absorbs blood cells and facilitates the body's natural healing process by providing a surface for fibrin and clot formation. The material swells to fill the access channel and block off the access site after the catheter body is removed. The outer layer 22 of stiffer collagenous material is formed on the outer surface of plug 10 to support the softer inner layer 20 and to form lumen 16. Lumen 16 is also lined with the stiffer, slower swell-rate collagenous material to ensure that swelling does not block off the lumen during positioning of the lumen near the vessel wall.

Plug 10 has a length, $L_1$, about 6–8 centimeters, selected to be longer than the expected depth of the femoral access channel so that a portion of the plug extends beyond the skin when the distal end of the plug is positioned adjacent the vessel wall. In this manner, the plug is easily slid distally over the access catheter into the access site by manually grasping the exposed portion. Further, once plug 10 is positioned within the access channel, the exposed portion of the plug can be grasped and pulled to adjust its depth or remove it from the channel, if desired, even after the introducer has been removed. The plug is generally made to be of sufficient length so the plug can be used on all patients without regard to weight, age, etc.

The outer diameter of plug 10 is generally selected to be slightly greater than the width of the access channel to prevent blood from leaking around the plug and into the surrounding tissue, but not so much greater as to cause tearing or excessive stretching of the tissue forming the wall of the channel. For example, for an access channel passing to the femoral artery a 9.5 French (outer diameter) access catheter (introducer) having a plug 10, between about 11–14 French (outer diameter) is used to occupy the channel. The inner diameter of the plug substantially corresponds to the outer diameter (SF) of the constant diameter portions of the access catheter. The proximal portion of plug 10 remains outside the access channel above the skin in use. As shown in FIGS. 1–4, the distal end of vascular plug 10 is bevelled at an angle of about 60° to ease entry into the body.

Figure 5A:
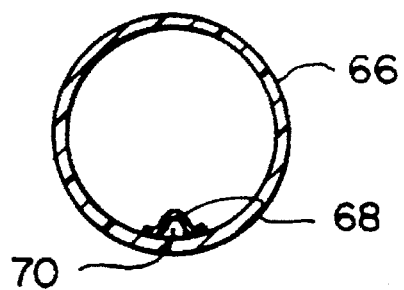
FIG. 5a shows the forming of the flow lumen of the plug.
Figure 5B:
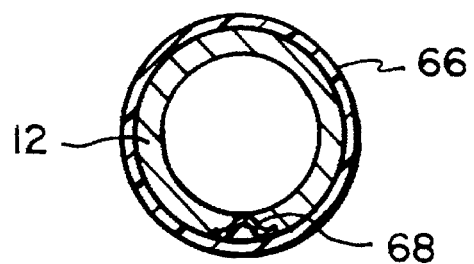
FIG. 5b shows the forming of the collagenous material of the plug.

Referring as well to FIGS. 5–5b, the construction of the vascular plug is described. As shown in FIG. 5, an outer shell 66 of relatively stiff material, for example, biodegradable plastic, gelatin, or, particularly, a less porous, slower-swelling collagenous material, is provided forming outer layer 22 of the plug. The stiffer material of shell 66 is kept thin (for example, 0.20 mm). A mandrel 70, shaped to provide a desired cross-sectional shape for lumen 16, is placed along an inner surface of the shell and a coating 68 of stiff collagenous material, like that of outer layer 22, is formed by dipping the shell into the collagen solution with mandrel 70 in place (FIG. 5a). After drying, mandrel 70 is removed leaving a stiff-walled U-shaped channel (lumen 16) formed along the inner wall of shell 66. Softer, spongier collagenous material, as described above, is formed within the tube to provide internal lumen 12 passing through its center (FIG. 5b). The spongier collagenous material may be provided as layered sheets of material or as a preformed cylinder that is compressed, positioned within the shell, and then released allowing it to spring against the wall of the shell.

The collagen selected for inner layer 20 softens relatively quickly (e.g. in about 15 seconds), begins swelling in about 1 minute after exposure to blood and is available under the name Colla-Tape from Integra LifeSciences, Plainsboro, N.J. Unlike the softer collagenous material the stiffer and denser material of outer tube may not begin to swell for periods of up to about one hour, but acquire a "tacky" characteristic in a much shorter time period which is advantageous for reasons discussed below in conjunction with FIG. 6d. The stiffness, as well as the swelling and degradation time of the collagenous materials, is generally a function of its porosity, which can be controlled by fabrication processes. For example, in fabricating the softer and spongier collagen material used for inner layer 20, the collagenous material is provided in a water slurry and frozen quickly. The ice is removed leaving a freeze-dried dispersion having large voided portions. Materials formed in this way have good hemostatic properties due to their porous nature which provides an increased surface area for allowing platelets to attach.

On the other hand, allowing the same collagenous material to air dry provides a stiffer, denser and less porous material suitable for outer coating 22. It is appreciated that other techniques for controlling the porosity of the collagenous materials may be used. Chemical treatments, including, for example, chemically treating the material with a cross-linking agent (e.g., glutaraldehyde) or treatment with ethylene oxide while exposing the material to heat may be used to provide collagenous materials with varying density and stiffness. Gelatins, which are denatured collagens, can also be used to provide stiff collagenous materials such as those available from Knox Gelatin, Inc., Englewood Cliffs, N.J. Hemostatic plugs are also described in U.S. patent application Ser. No. 787,518 by J. R. Haaga, filed Nov. 4, 1991, Ser. No. 896,588 also by Haaga, filed Jun. 10, 1992, and U.S. Pat. No. 4,838,280. The entire contents of all of these cases is hereby incorporated by reference.

Both the inner 20 and outer layer 22 degrade within the body and are completely dissolved after about thirty days. A thin coating (not shown) of gelatin may be placed at the interface between the two layers to provide adhesion. A lubricant, for example a hydrogel or silicone, may be placed on the catheter body and, likewise, on the exterior surface of the tube 66 to reduce friction when sliding the plug into the body. The plug may have mechanical or pharmaceutical properties selected for a particular application.

Use

Figure 6:
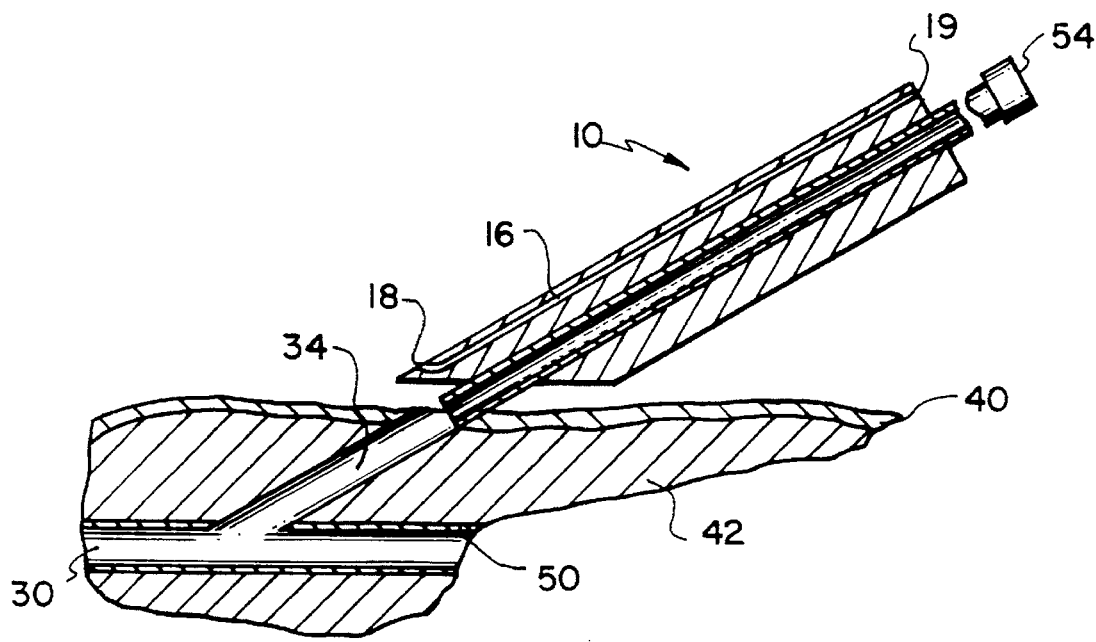
FIG. 6 shows the plug and access catheter prior to insertion within the incision channel.
Figure 6A:
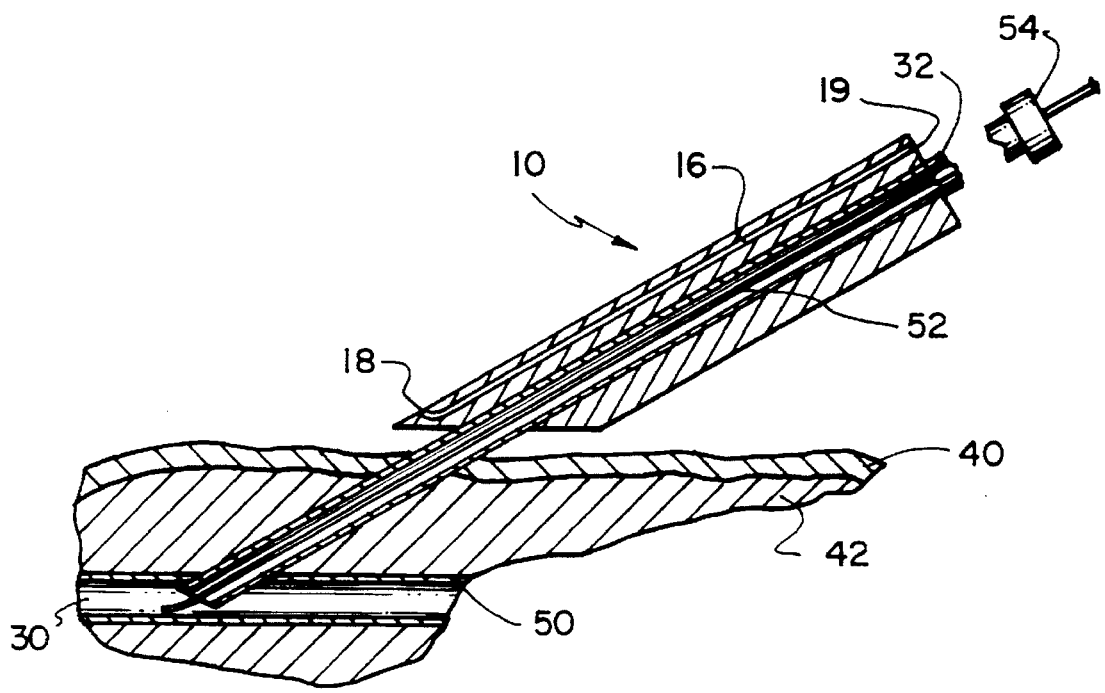
FIG. 6a shows the insertion of the access catheter within the incision channel.
Figure 6B:
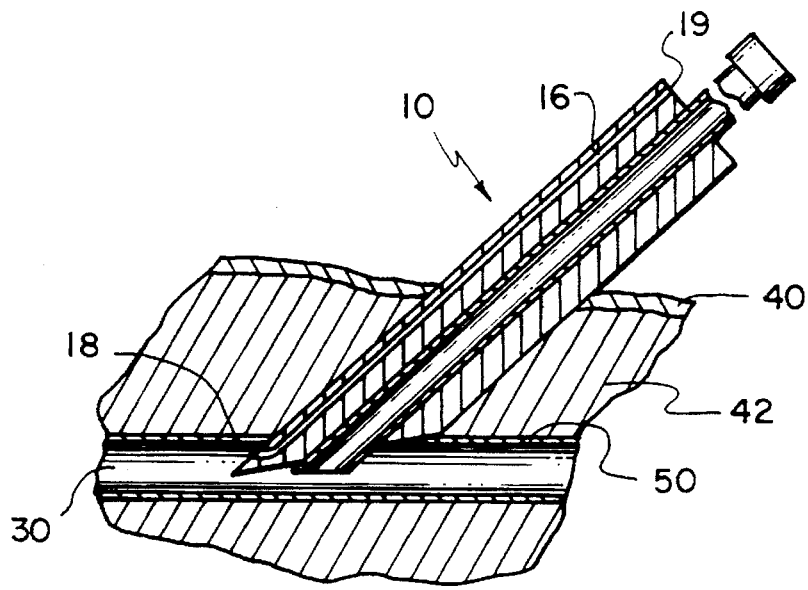
FIG. 6b shows the insertion of the plug over the access catheter and within the incision channel.
Figure 6C:
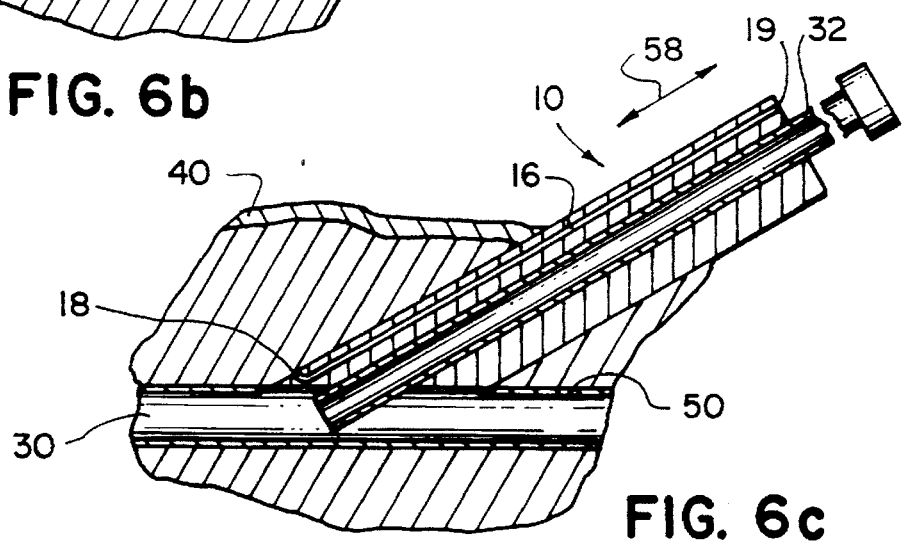
FIG. 6c shows the positioning of the plug within the incision channel.
Figure 6D:
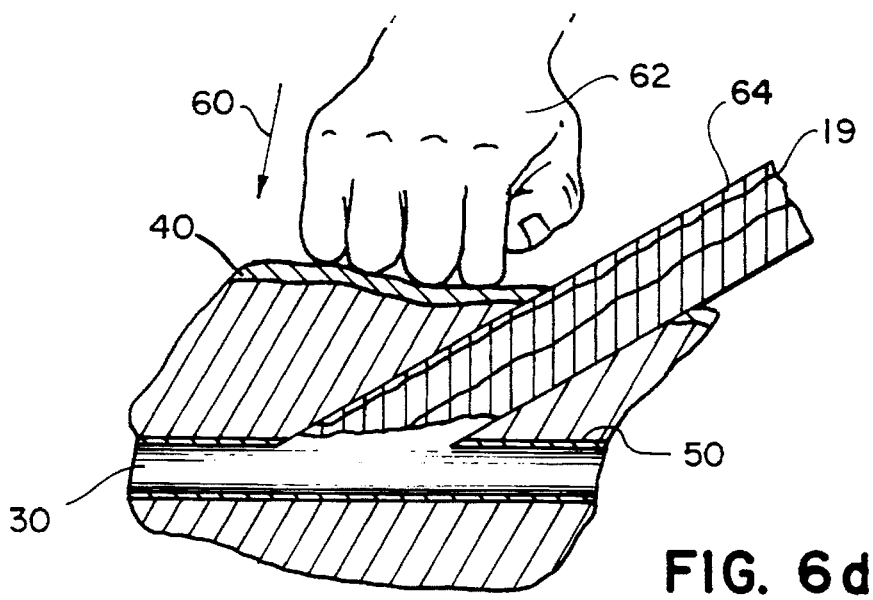
FIG. 6d shows the plug within the incision channel with the access catheter removed.

Referring now to FIGS. 6–6d, an access channel may be treated using the vascular plug of FIGS. 1–4, as follows. An access channel 34 to the femoral artery is formed by making an incision with a thin needle that punctures the tissue which is then widened into an access channel using dilators. The access channel, therefore, is characterized as a rip or tear of the tissue. The walls of the incision rebound to fill the incision opening unless a plug such as the access catheter is provided in the incision to push the walls outwardly. As shown particularly in FIGS. 6 and 6a, vascular plug 10 is slid axially over an access catheter 32 (e.g. 8 French) and positioned at a proximal portion of the catheter 32 outside the body.

Referring to FIG. 6a, with the plug near the proximal end of the access catheter, the access catheter 32 is positioned in access channel 34 through tissue, including skin 40 (usually about 0.25 inch thick), underlying fascia 42 (usually about 1–2 inch thick) and the wall 50 (usually about 1 mm thick) of the artery (about 6–10 mm lumen diameter). Prior to inserting the plug, anticoagulants may be delivered through the access catheter to inhibit clot formation in the artery. A guidewire 52 is passed through the access catheter 32 and into artery 30 for directing diagnostic or therapeutic catheters (e.g. angioplasty balloon catheters during the operation). A valve 54 at the proximal end of access catheter 32 can be opened to deliver these medical devices.

Referring to FIG. 6b, at the completion of the catheterization procedure, plug 10 is slid axially down the access catheter and into access channel 34. As illustrated, the plug is initially positioned such that access opening 18 is within artery 30 and blood flows through lumen 16. Although the physician cannot, of course, see the distal end of plug 10, its location within the artery is indicated by blood flow, which is delivered through access opening 18 and through the lumen 16 to opening 19 at the proximal end of the plug. Plug 10 may also be rotated while in the blood vessel, to assure that access opening 18 is not pressed against and occluded by the wall, giving a false indication that the opening is in the access channel. In some cases, insertion may be facilitated by positioning the pointed tip below the catheter and upon reaching the area near the vessel wall, rotating the plug 180°. A dilator can be provided within the introducer catheter to provide lateral support during delivery of the plug into the access channel.

Referring to FIG. 6c, plug 10 is moved proximally until access opening 18 is located within the access channel 34. The wall of the access channel seals against the access opening and prevents the flow of blood through it. This condition is visually indicated by the cessation of blood flow at the proximal end of the plug. Plug 10 is iteratively moved proximally and distally (arrow 58) to accurately locate access opening 18 at a depth adjacent wall 50 of the artery 30 by observing the flow of blood and lack thereof. While not necessary in all cases, access catheter 32 may also be rotated about its axis to rotationally orient the catheter so the distal end of plug 10 can in turn be rotationally oriented. Note that in this embodiment, access opening 18 is formed near the most distal portion of the plug so that detection of blood can be achieved with minimal intrusion of the plug within the vessel. This is desirable to minimize the risk of tearing the vessel wall and to limit the amount of hemostatic material introduced within the vessel.

Referring to FIG. 6d, once plug 10 is accurately positioned such that the distal end of the plug is located adjacent the vessel wall 50, access catheter 32 is removed from the access channel by drawing it axially distally, and manual compression is maintained over the plug (arrow 60, hand 62) for a period of about five minutes. As shown in FIG. 6d, during the period in which manual compression is applied, the collagenous material of the inner layer 20 becomes saturated and swollen with blood and both internal lumen 14 and lumen 16 are occluded. As described above, the stiffer materials used for forming outer layer 22 and lumen 16 take substantially longer to swell than inner layer 20. However, in a relatively short time these stiffer collagenous materials acquire a sticky condition so that when manual compression is applied to the plug and lumen 16, the walls of lumen 16 adhere thereby occluding the lumen and preventing subsequent blood flow out of the plug. Thus, the stiff outer walls of lumen 16 maintain a clear passage for blood flow during the period the physician is positioning the plug, with minimal swelling, and after proper positioning can effectively be sealed to prevent blood flow.

Guidewire 52 may be removed before or after catheter 32 is removed. One advantage of maintaining the guidewire in the body throughout most of the operation is that the catheter can be easily removed and then replaced if it becomes desirable.

With the access catheter 32 completely removed, a proximal portion 64 of the plug 10 still extends out of the access channel. If the distal end of the plug has been improperly positioned such that it extends into the artery 30, the plug can be removed from the access channel without surgery, by pulling proximally on the exposed portion 64. Typically, using a two layer plug as discussed above, the protective plug can be removed up to 3 hours after implantation, a time after which the portions of the protective plug within the body degrade beyond the point which they can be removed as a unit by pulling axially on the exposed portion 64. As mentioned above, the effective removal time can be varied by using different types of materials in the plug.

After the waiting period to ensure that there are no complications, portion 64 of the protective plug extending beyond the skin is cut off with forceps with portions remaining in the channel degrading over time.

Other Embodiments

Figure 7:
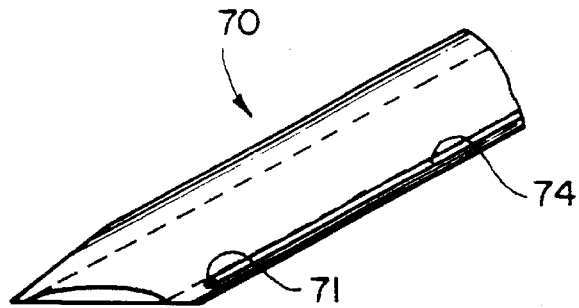
FIG. 7 is a perspective view of another plug for treating an access channel.
Figure 8:
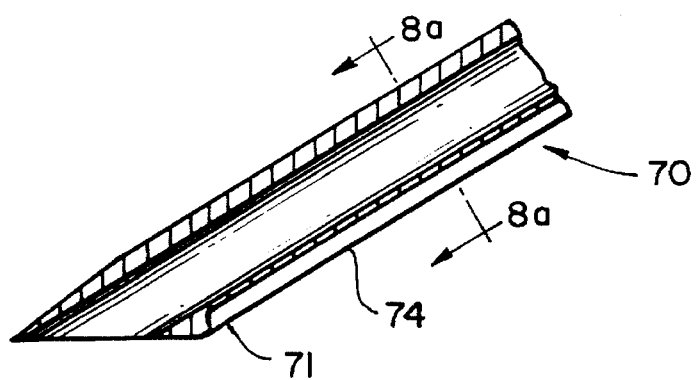
FIG. 8 is a cross-sectional side view of the plug of FIG. 7.
Figure 8A:
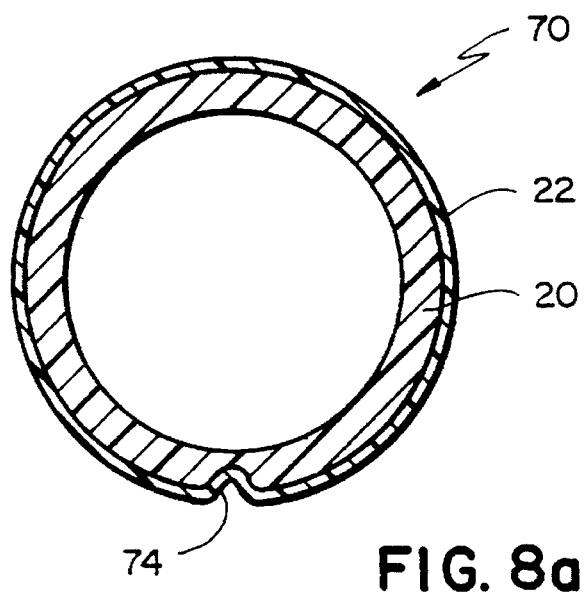
FIG. 8a is an enlarged end-on cross-sectional view along line 8a—8a in FIG. 8.

Referring to FIGS. 7, 8 and 8a, a plug 70, is tapered to provide an irregular conical configuration at its distal end that facilitates insertion. The plug 70 also includes an open flow channel 74 disposed along its outer surface. The flow channel extends from a distal extremity 71 at a location proximal of the taper to the proximal end of the plug. In use, the blood flows through the channel when the extremity 71 is inside the blood vessel; the flow path is thus defined by the channel but is bordered in part by the tissue on the channel wall opposite the channel. The cross-sectional geometry of the channel is oblong or U-shaped with the width being less than the depth so that the portions of the plug adjacent the tissue wall are prevented from excessive prolapse into the channel which could block blood flow. Alternatively, it may be desirous to provide cross-sectional geometries, such as triangular or hourglass cross sections. An outer stiff layer 22 lines the flow channel and prevents the softer and swellable collagenous material of the plug from obstructing the channel during positioning in the access channel.

Figure 9:
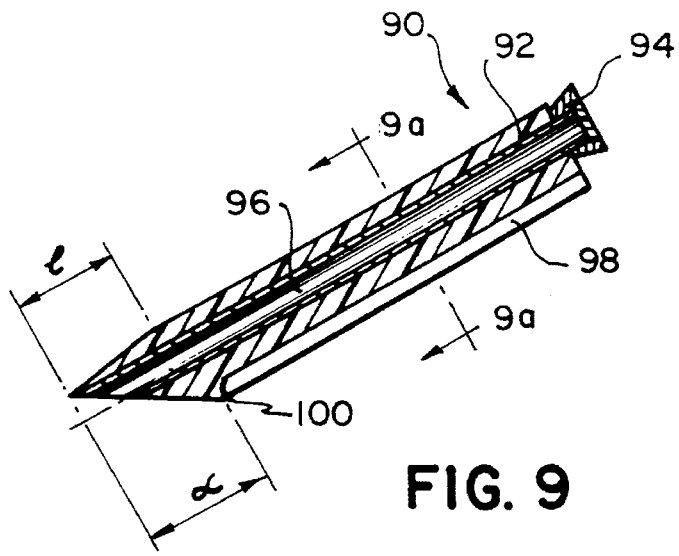
FIG. 9 is a cross-sectional side view of another plug for treating an access channel.
Figure 9A:
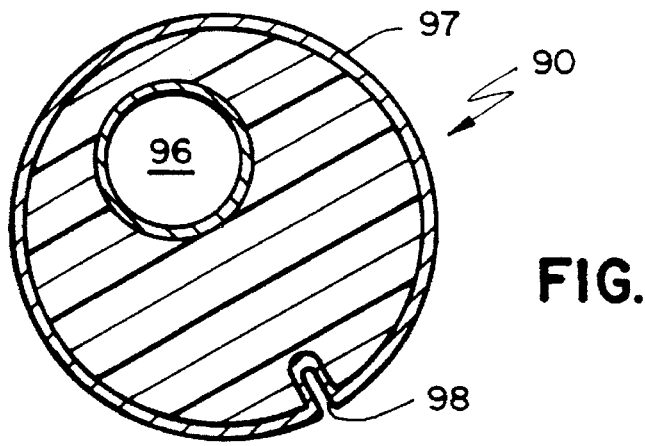
FIG. 9a is an enlarged end-on cross-sectional view along line 9a—9a in FIG. 9.
Figure 9B:
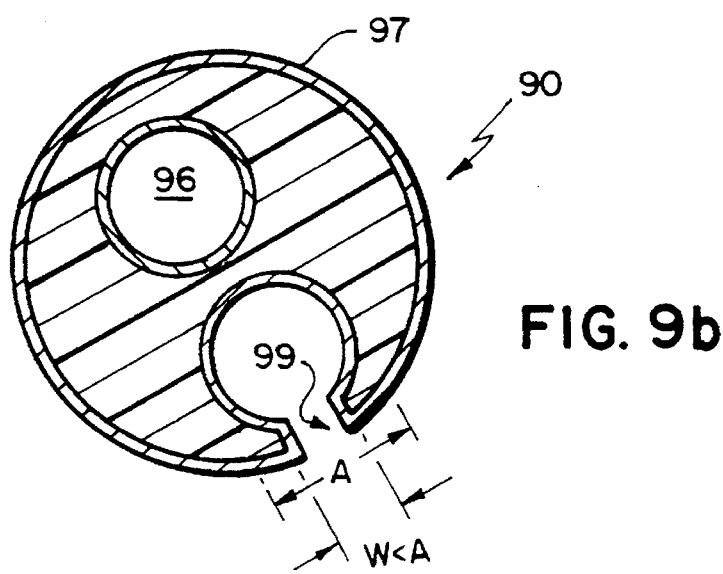
FIG. 9b is an enlarged end-on cross sectional view of another embodiment of the plug in FIG. 9.

In a further embodiment, as shown in FIGS. 9 and 9a, in a system of delivering a hemostatic material to an incision channel, the plug and introducer device are provided within the access channel simultaneously. Vascular plug 90 is provided over the introducer device 92 or a fascial dilator, having a valve 94 at its proximal end for allowing the plug to be introduced over a guidewire or delivery over other medical devices (e.g., angioplasty balloon catheters). Vascular plug 90, supported by dilator 92, is used to open and widen the incision of the access channel and includes both an inner lumen 96 for receiving dilator 92 and a flow channel 98 disposed along the outer surface of the plug and spaced from the distal end of the plug by a thin wall 100. A stiffer collagenous coating 97 is provided over both plug 90 and flow channel 98. For example, the cross-sectional geometry of the channel is preferred to be selected so that the depth of channel 98 is greater than the width. For example, referring to FIG. 9b, in embodiments, flow channel 99 includes a portion along the outer surface of the plug with a narrow width (W) which opens into a larger opening having a width (A) within the plug. By maintaining width (W) less than width (A) the possibility of loose pieces of tissue, or prolapsing tissue, from the access channel wall obstructing the channel is minimized.

In this embodiment inner lumen 96 is offset from the center of plug 90 in order to provide a greater wall thickness between the inner lumen and the flow channel. In applications where the time before swelling is desired to be extended, plug 90 may be formed of other wound-healing materials having stiffness characteristics intermediate that of the spongier collagen used for the inner layer of the plug and the stiffer coating used for the outer layer of the flow channel and plug as described above. For example, plug 90 may be formed of a stiffer biodegradable polymer, such as polyglycolic acid, that is seeded with a collagen or thrombin to provide the plug with hemostatic properties.

Figure 10A:
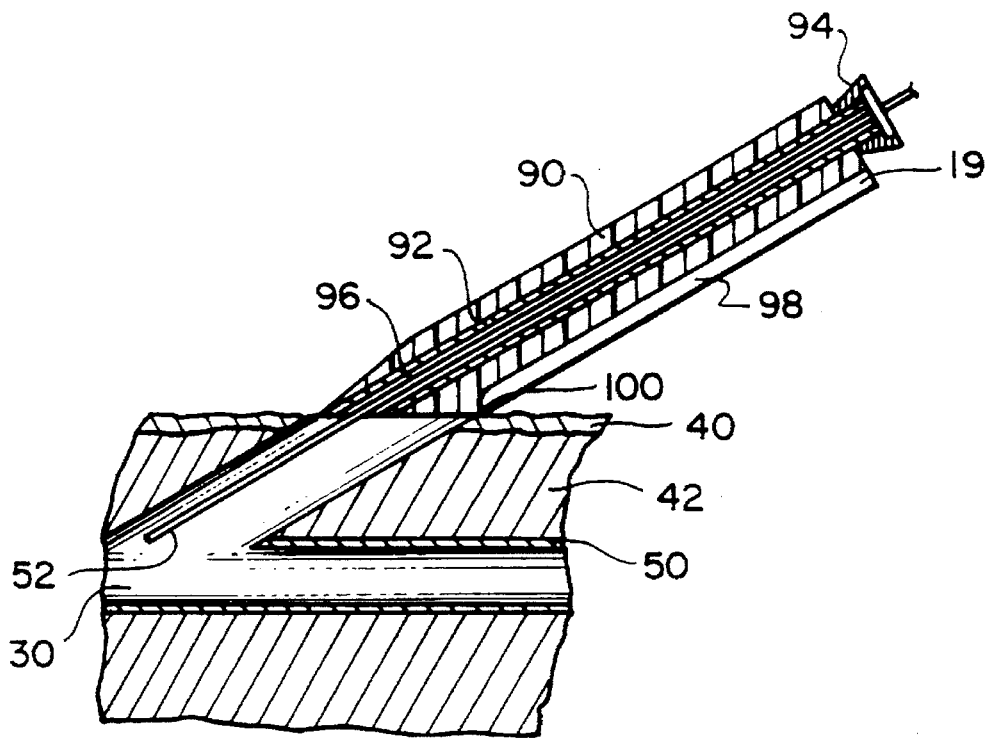
FIG. 10a shows the insertion of the access catheter within the incision channel.
Figure 10B:
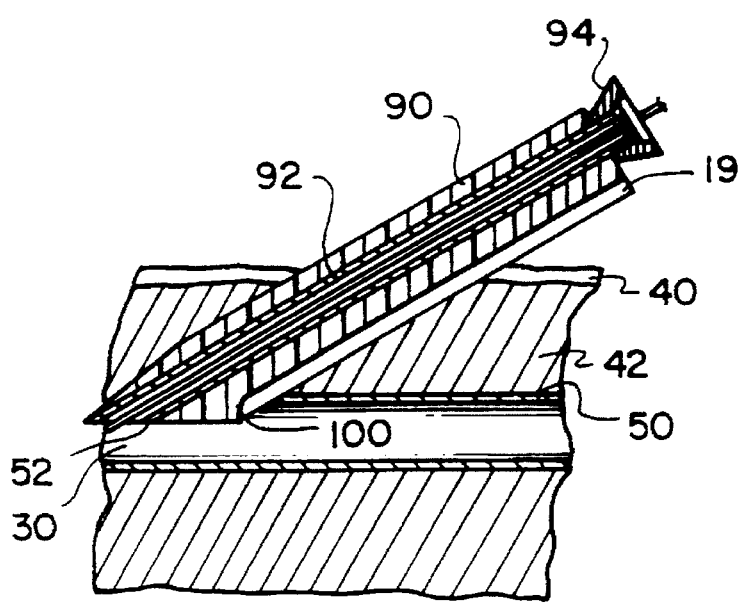
FIG. 10b shows the insertion of the plug over the access catheter and within the incision channel.
Figure 10C:
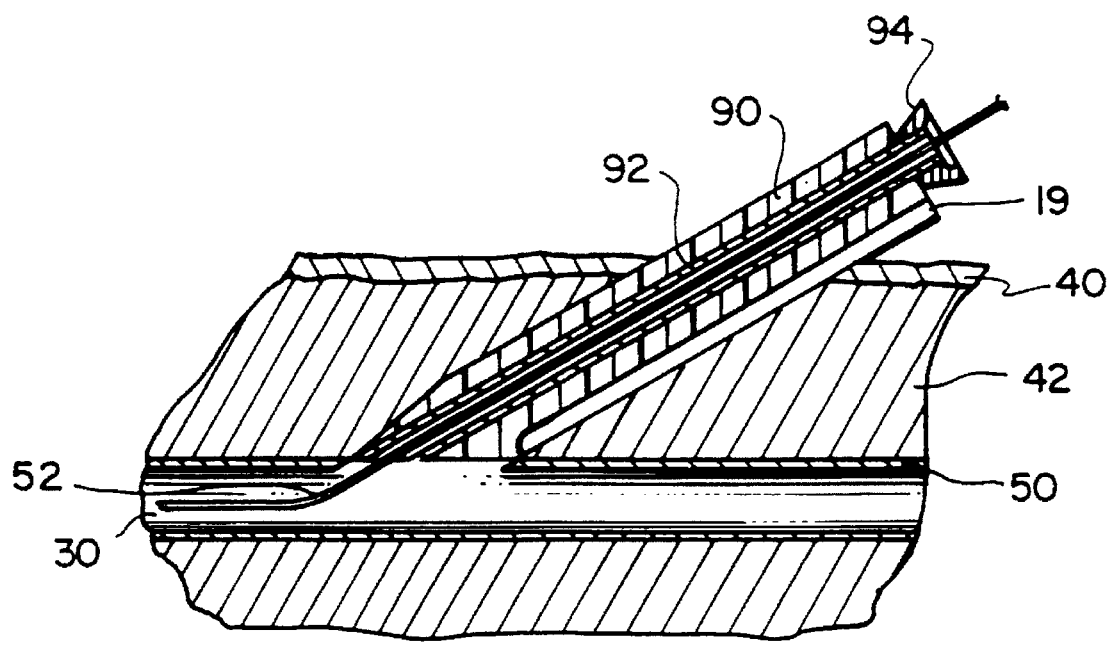
FIG. 10c shows the positioning of the plug within the incision channel.
Figure 10D:
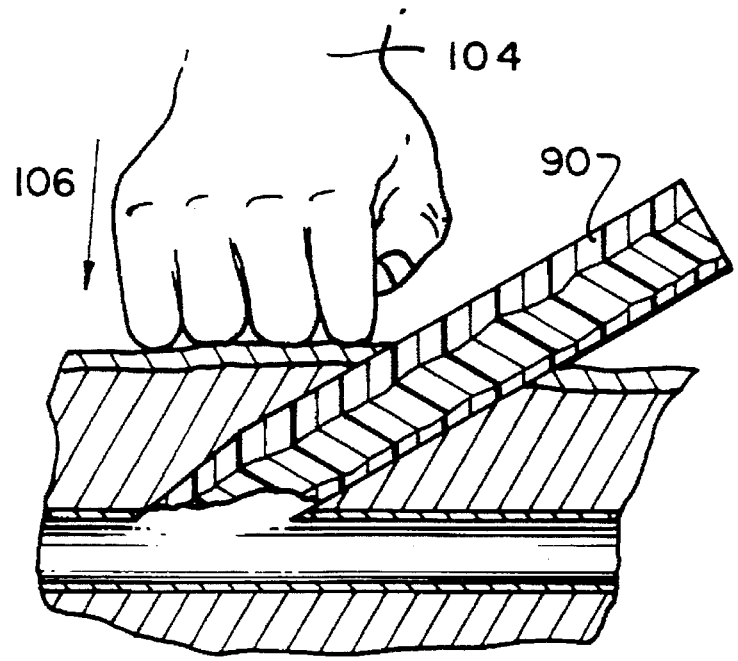
FIG. 10d shows the plug within the incision channel with the access catheter removed.

Referring to FIGS. 10–10c, vascular plug 90 is shown surrounding a catheter 92 having a length substantially that of the length of the plug and a beveled distal end consistent with that of the plug. Catheter 102 may have a relatively small diameter with sufficient rigidity for guiding plug 90 within the access channel. Alternatively, the catheter may be of larger diameter, as shown here, for introducing through valve 94 other medical devices. Plug 90 and catheter 92 are pushed together, as an assembly, over pre-inserted guidewire 52 and through the skin tissue 42 until the distal end of channel 98 is within the artery 30 allowing blood to flow through the channel to the proximal end of plug 90 above the skin level (FIG. 10a). Referring to FIG. 10b, plug 90 and catheter 92 are iteratively moved in the axial direction until wall 100 is positioned adjacent the vessel wall 50 and flow channel 98 is entirely within the access channel. With plug 90 properly positioned, other diagnostic or therapeutic catheters can be introduced through catheter 92 and the medical procedure performed. After the procedure is completed catheter 92 is removed from the access channel leaving plug 90 in place. As was the case, in the embodiments of FIGS. 6–6d, manual compression (arrow 106) from the physician's hand 104 is applied to the plug until sufficient fibrin and clot formation provides a barrier to blood flow from the artery (FIG. 10c).

Figure 11:
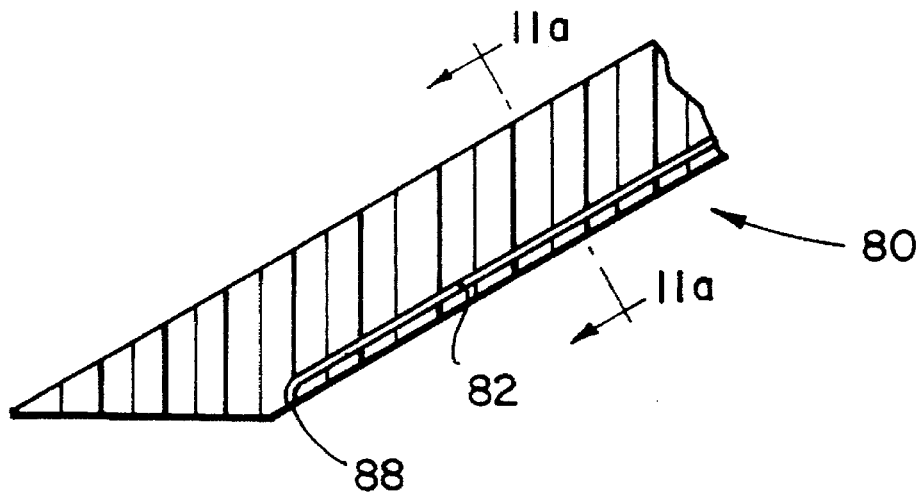
FIG. 11 is a cross-sectional side view of another plug for treating an access channel.
Figure 11A:
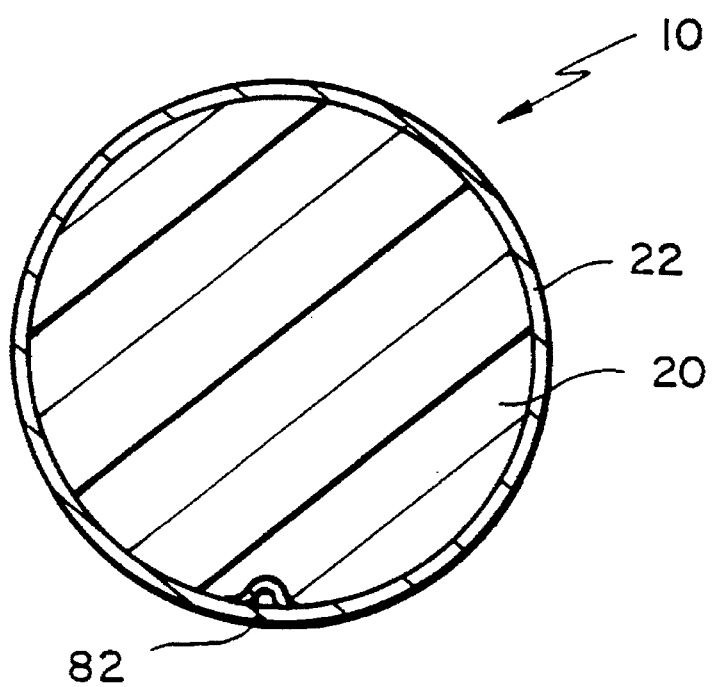
FIG. 11a is an end-on cross-sectional view along line 11a—11a in FIG. 11.

Referring to FIGS. 11 and 11a, in another embodiment, vascular plug 80 does not employ a directing device for positioning the plug. Thus, plug 80 does not include an internal lumen for delivering the plug over a directing device. Plug 80 includes lumen 82 formed as described above in conjunction with FIGS. 5–5b which extends from an access opening 84 at the distal end of the plug to the proximal end of the plug extending out of the body.

Figure 12A:
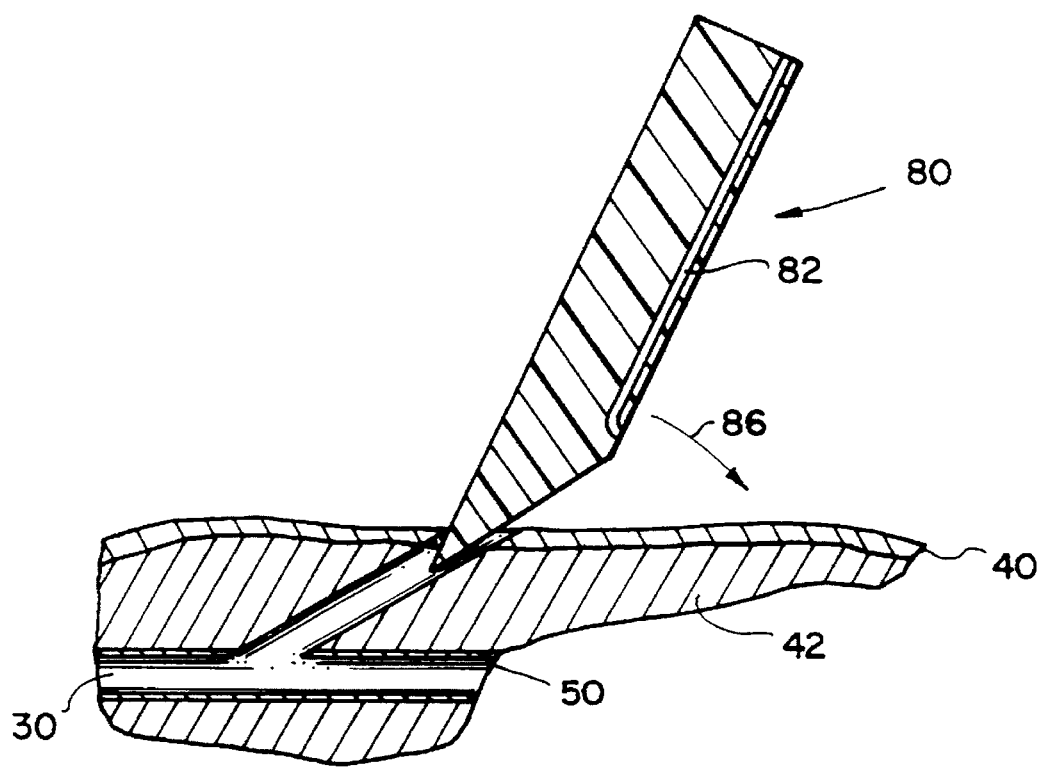
FIG. 12a shows the insertion of the access catheter within the incision channel.
Figure 12B:
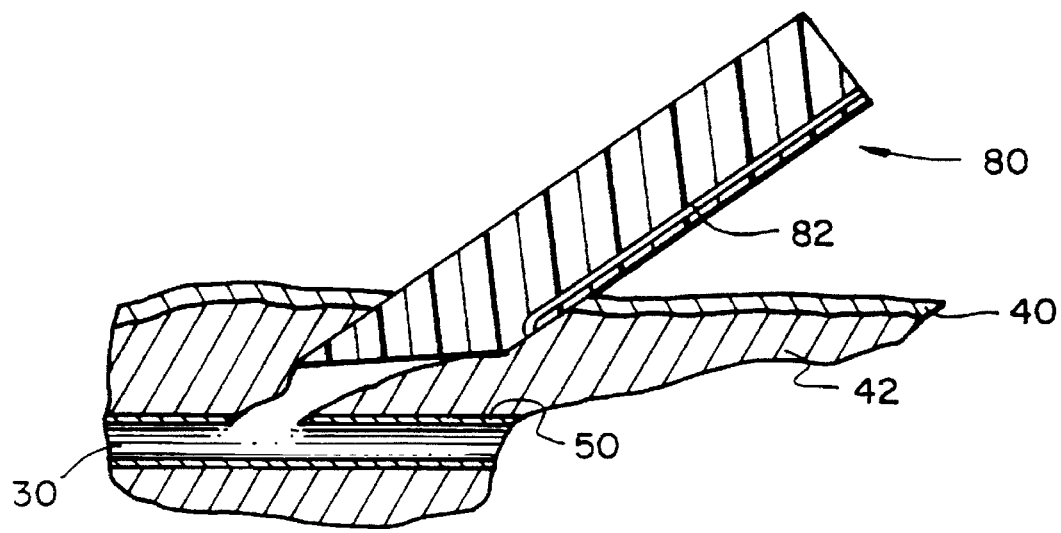
FIG. 12b shows the insertion of the plug over the access catheter and within the incision channel.
Figure 12C:
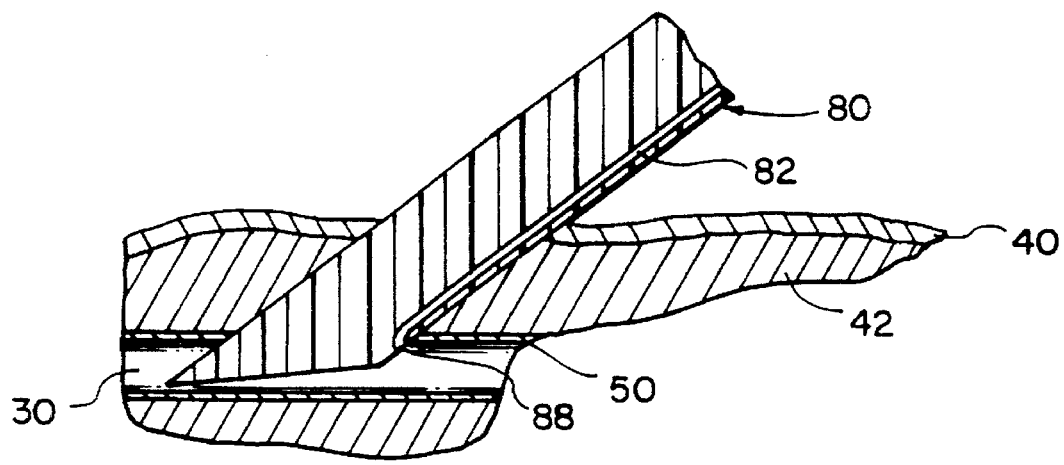
FIG. 12c shows the positioning of the plug within the incision channel.
Figure 12D:
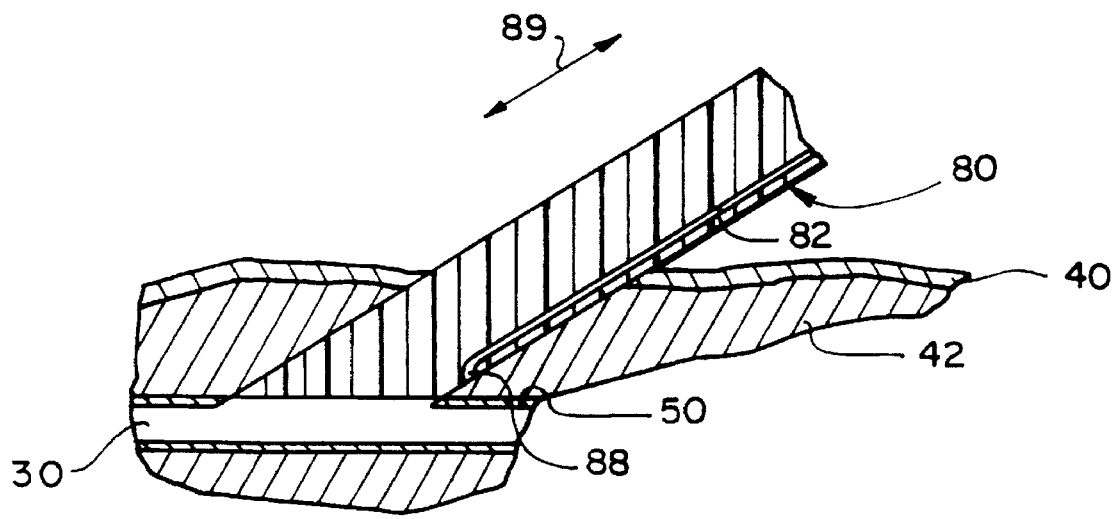
FIG. 12d shows the plug within the incision channel with the access catheter removed.

Because a directing device (e.g., access catheter) is not used to introduce plug 80 within the access channel, the plug itself is used to push the walls of the access channel outward through the skin, underlying fascia and the wall of the artery. For example, referring to FIG. 12, plug 80 is initially positioned such that the distal end of the plug is tilted into the incision and then pivoted (arrow 86) to align the angle of the plug with the angle of the channel for further insertion into the channel (FIG. 12a). It is generally desired that the outer collagen coating lining the flow path be selected from a material which softens, but retains its rigidity for a sufficient time (e.g. about 1 minute) for positioning the plug. Plug 80 is moved proximally until access opening 88 is within the access channel to stop the flow of blood through lumen to opening 19 (FIG. 12b). As shown in FIG. 12c, plug 80 is iteratively moved (arrow 89) proximally and distally until access opening 88 is properly located by observing the flow of blood and lack thereof at the opening. After the physician is satisfied that plug 88 has been properly positioned, manual compression is applied for a sufficient time to allow the plug to swell and degrade to the point that blood flow is cut off. In this embodiment, the flow channel 82 and opening 88 are along the short side of the plug. Although a greater portion of the diameter is introduced within the vessel before the flow of blood is detected, channel 74 at the distal end of the plug is surrounded by a greater amount of material, providing better support and stronger construction, that is less susceptible to damage as the plug is inserted into tissue.

Figure 13:
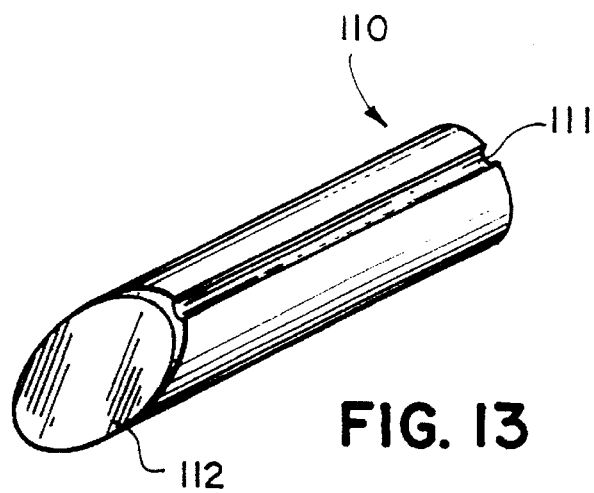
FIG. 13 is a perspective view of another hemostatic plug.
Figure 14:
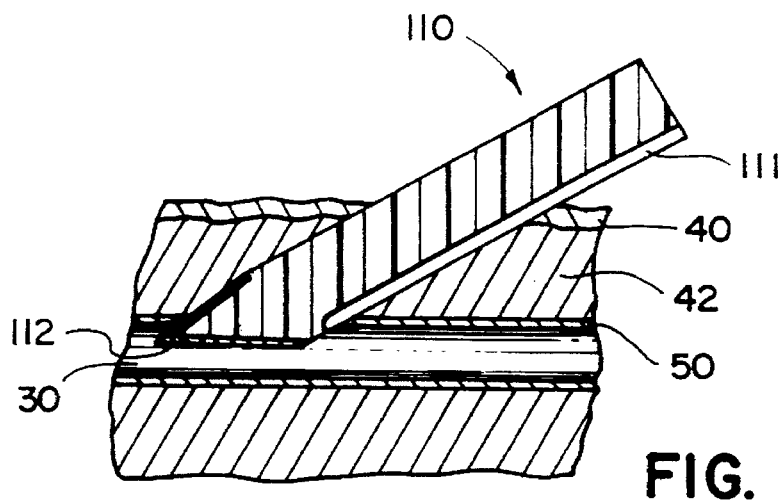
FIG. 14 illustrates the use of the plug of FIG. 13.
Figure 14A:
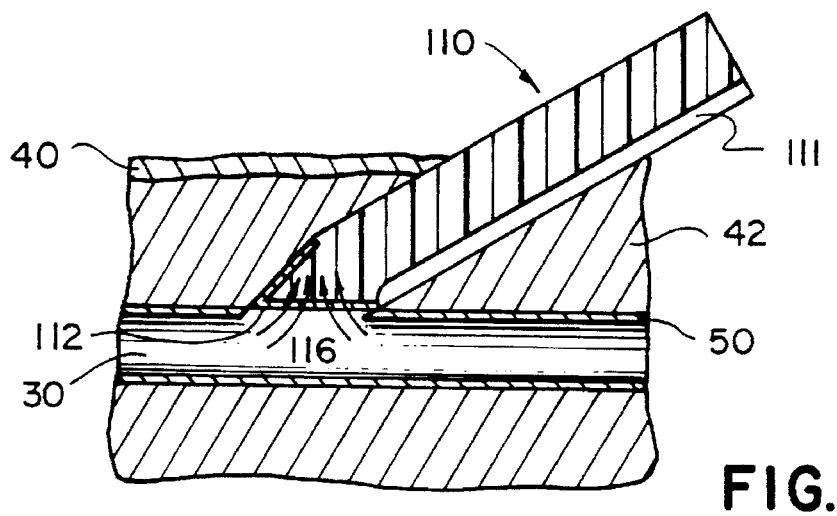
FIG. 14a is a second illustration of the use of the plug of FIG. 13.

Referring to FIG. 13, a vascular plug 110 includes a lumen 111 and a distal portion having an outer coating 112 formed of a stiffer collagenous material with low hemostatic properties formed over softer collagenous material. In the embodiment shown in FIG. 13, with the flow channel on the short side of the plug, more of the plug may be located inside the artery during positioning. With this arrangement, the distal portions of the plug include a stiffer, less hemostatic coating so that the more hemostatic, softer material of the plug is generally not exposed within the artery during positioning of the plug, as shown in FIG. 14. In time, as shown in FIG. 14a, the slower-swelling low hemostatic coating 112 degrades allowing blood to saturate the softer, spongier hemostatic material of the plug (arrows 116). In other embodiments, the plug does not include any stiff outer coatings. In these embodiments, because the plug does not include an outer coating for enclosing the flow channel, greater care must be taken by the operator to ensure that surrounding tissue does not move into the channel and block the flow of blood to the proximal end of the plug. In addition, because the plug is formed entirely of soft collagen material, the plug must be positioned before the material swells to the degree that fibrin and clot formation begins and the channel breaks down.

Figure 15:
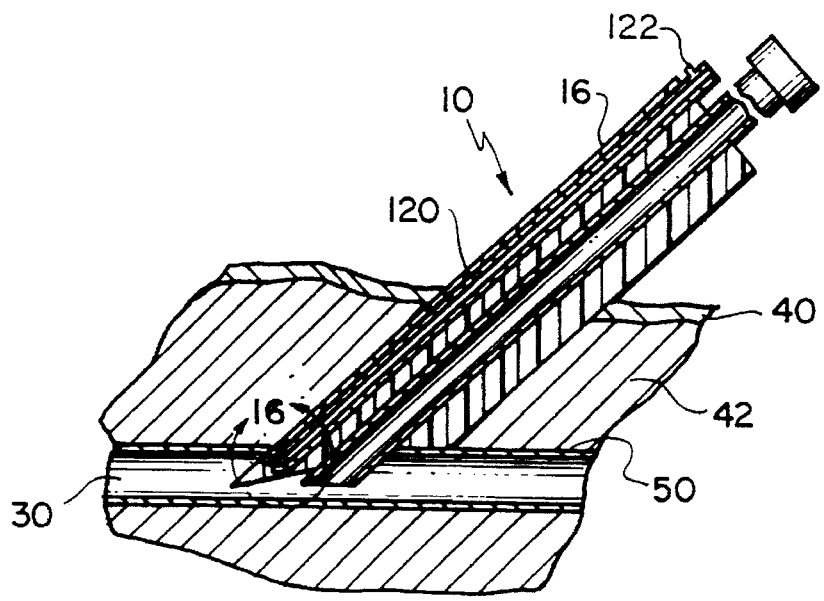
FIG. 15 illustrates the use of another plug for treating an access channel.
Figure 15A:
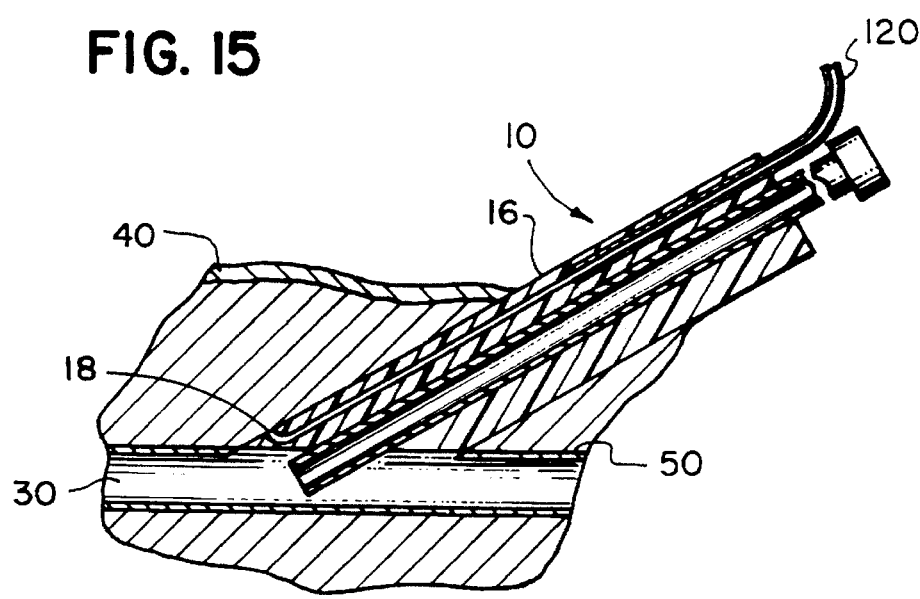
FIG. 15a is a second illustration of the use of another plug for treating an access channel.
Figure 16:
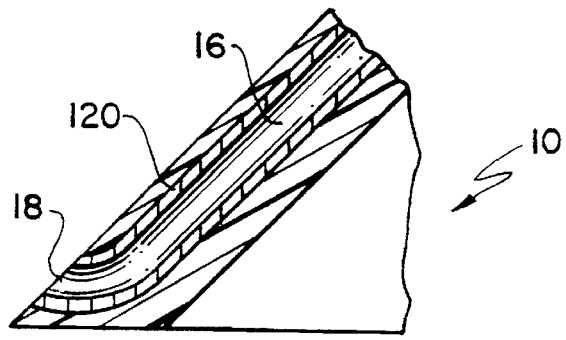
FIG. 16 is an enlarged view of the distal tip end of the plug within line 16—16 in FIG. 15.

Referring to FIGS. 15–15a, and 16, in another embodiment, a flexible, nondegradable support tube 120 is provided within lumen 16 to define the lumen as shown constructed in FIGS. 5–5b. Support tube 120 may be fabricated from plastic, such as polyethylene, or metal, such as nitinol hypotubing, to ensure that the softer, faster swelling collagen material of the plug does not block off lumen 16 during positioning of the plug within the access channel. Support tube 120 is slid into the lumen prior to the insertion of the plug into the access channel, and as shown in FIG. 16, extends to opening 18 at the distal end of the plug. In a preferred embodiment, a stop 122 is formed along the outer surface of the tube at its proximal end so that the support tube can be slid into a preferred lumen in the plug and positioned so that it does not extend beyond opening 18. Referring to FIG. 15, support tube 120 remains within lumen 16 during the time plug 10 is being positioned within the channel and allows, when access opening 18 is within the vessel, blood to flow freely to the proximal end of the plug. When the physician is satisfied that the plug is properly positioned, support tube 120 as well as access catheter 32 are removed and manual compression is applied to the plug (FIG. 15a). Although in this embodiment the entire plug is fabricated from a soft collagenous material, a stiffer outer coating for lining lumen 16 (as described above in conjunction with FIGS. 5–5b) may also be provided. In embodiments, support tube 120 can be replaced with a length C-shaped tube suitable for lining a flow channel, as described above in conjunction with the embodiments of FIGS. 7–10.

Figure 17:
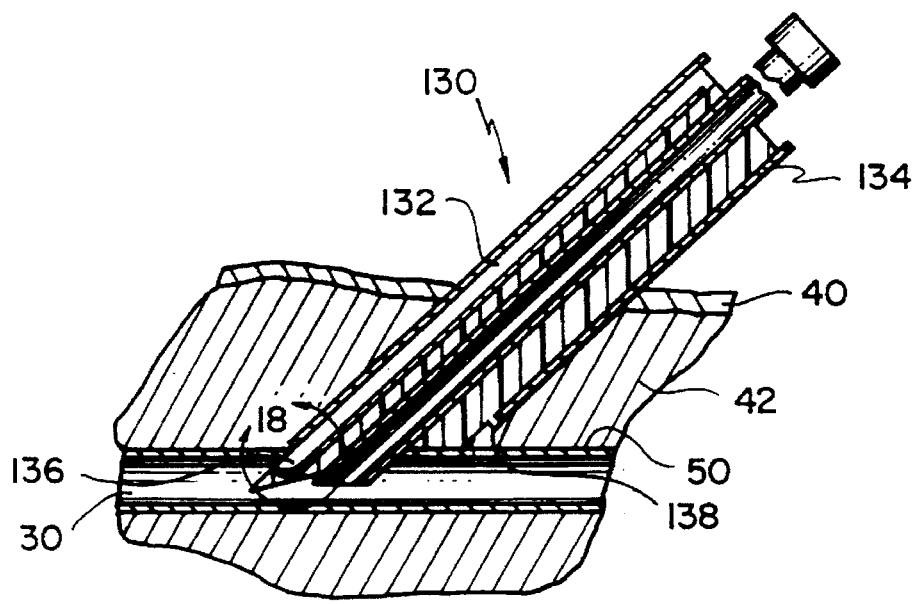
FIG. 17 illustrates the use of another plug for treating an access channel.
Figure 17A:
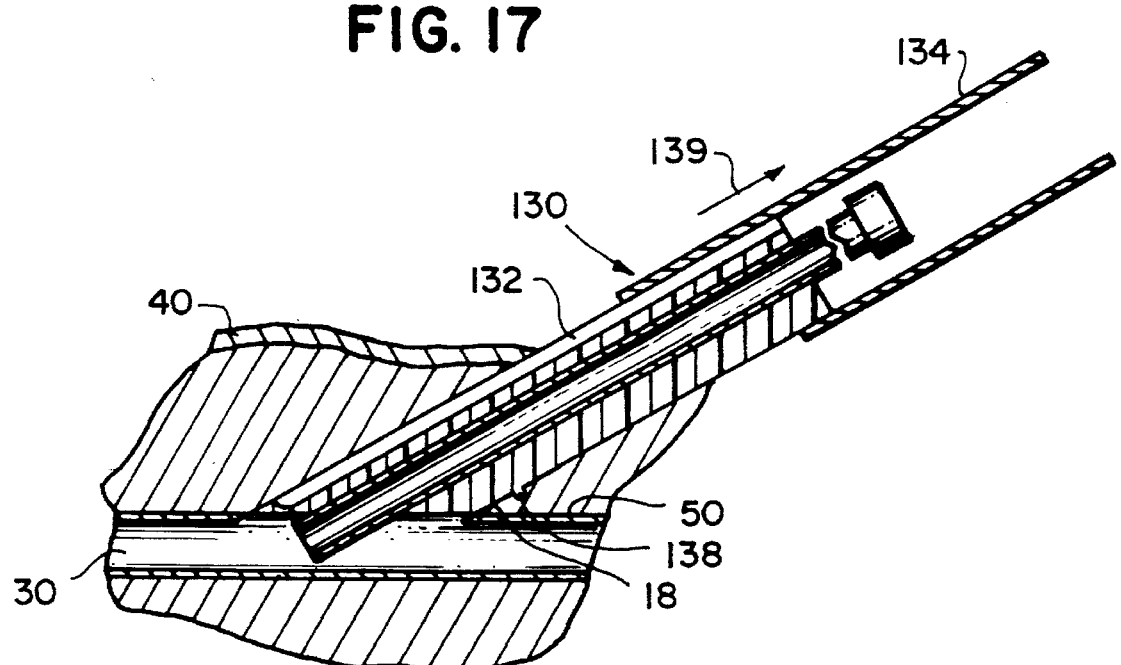
FIG. 17a is a second illustration of the use of another plug for treating an access channel.
Figure 18:
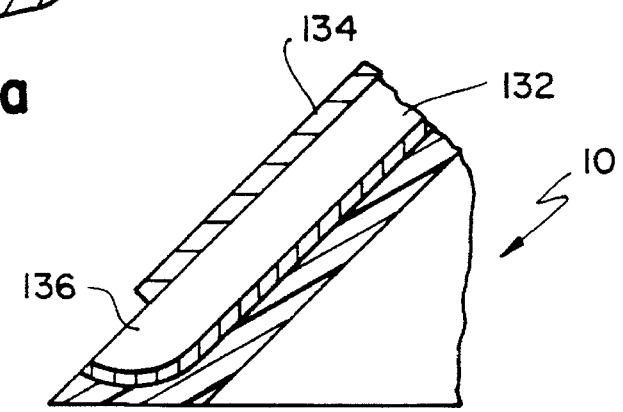
FIG. 18 is an enlarged view of the distal tip end of the plug within line 18—18 in FIG. 17.

In another embodiment a plug can be provided with a removable plastic sheath. As shown more particularly in FIGS. 17 and 18, plug 130 includes an exposed flow channel 132 disposed along the outer surface of the plug. A removable plastic sheath 134 is positioned over the plug, prior to insertion within the access channel, to enclose channel 132 and to provide a small opening 136 at the distal end of the plug. A stop 138 may be formed along the outer surface of the shortened side of the plug to prevent the sheath from extending beyond opening 136 during manipulation of the plug. Removable plastic sheath 134 ensures that the channel remains unobstructed during positioning of the plug of tissue from the access channel or from swelling of the plug. As shown in FIG. 17a, when plug 130 is satisfactorily positioned, the physician slides the plastic sheath off of the plug (arrow 139). The physician then applies manual compression to the plug to close off channel 132.

Figure 19:
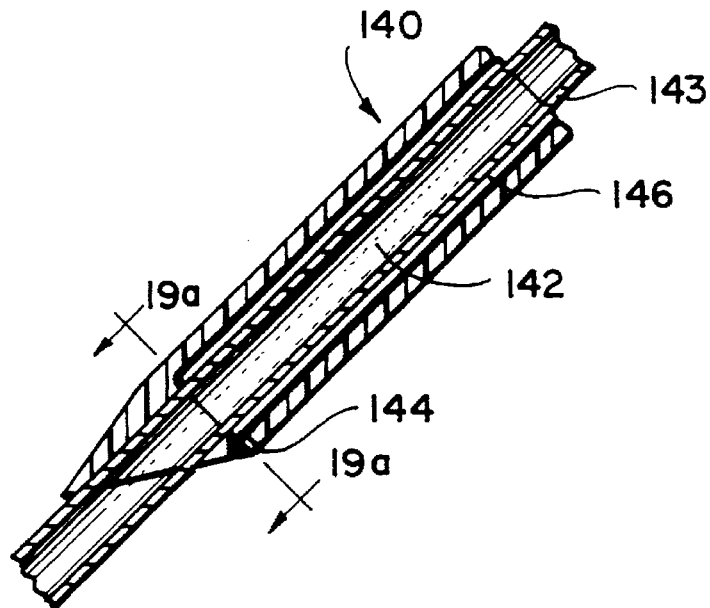
FIG. 19 is a cross-sectional side view of another plug for treating an access channel.
Figure 19A:
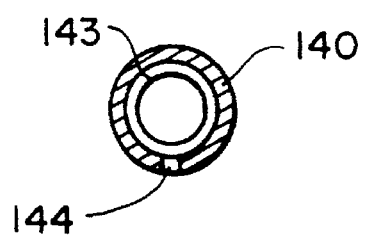
FIG. 19a is an end-on cross-sectional view along line 19a—19a in FIG. 19.

Referring to FIGS. 19 and 19a, a plug 140 utilizes a dual-purpose inner lumen 142 to not only receive an introducer catheter 143 but to also provide a flow channel from a side opening 144 at the distal end of the plug to the proximal end of the plug. In this embodiment, internal lumen 142 has an inner diameter, at the distal end of the plug, that is approximately that of the outer diameter of the introducer catheter. Plug 140 has a larger diameter from side opening 144 to the proximal end of the plug, thereby providing a flow channel 146 defined by a space between the inner wall of the plug and the introducer catheter. In other variations of this embodiment, the widened diameter may narrow again at the proximal end of the plug to a diameter consistent with that of the outer diameter of the plug with an exit port at the proximal end to allow fluid flow out of the plug. The reduced diameter at the proximal end of the plug provides additional support to the introducer catheter and allows the catheter to be more centrally located within the plug.

Figure 20:
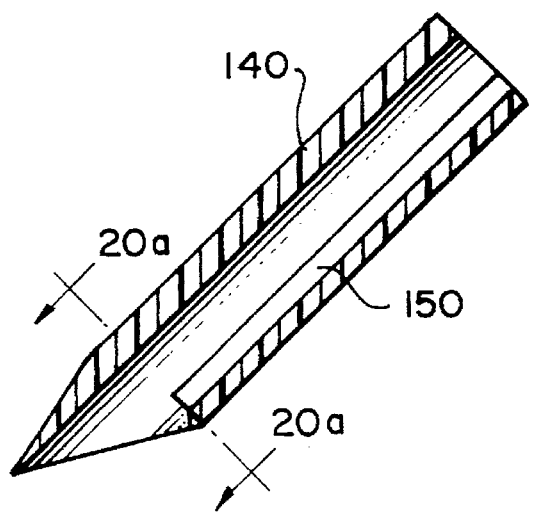
FIG. 20 is a cross-sectional side view of an alternative embodiment of a plug for treating an access channel.
Figure 20A:
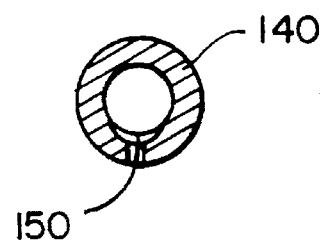
FIG. 20a is an end-on cross-sectional view along line 20a—20a in FIG. 20.

In the embodiment as shown in FIGS. 20 and 20a, a channel 150, having a semicircular shape, extends from the distal end of the plug (introducer catheter removed) where opening 144 is positioned to the proximal end of the plug. Unlike the embodiment described above in conjunction with FIG. 17, the inner diameter of channel 150 is approximately that of the outer diameter of an introducer catheter except in the region where channel 150 is provided.

Still other embodiments are within the following claims. For example, referring again to FIG. 1, any of the vascular plugs of the embodiments described above may include a series of measurement marks 160 running distally along their outer surfaces to indicate the distance from the opening 18. The marks, which may be numbered to indicate distance (numbers not shown), can be used to measure the actual depth of the access channel by noting the mark adjacent the surface of the skin when the opening is located adjacent the vessel wall. This feature is particularly useful where the plug is desired to be moved and then repositioned to its original desired location after the plug has been disposed within the access channel for several minutes and substantial swelling has occurred. The plug may also include an axially oriented alignment mark 162 to select and maintain the rotational orientation of the plug. The marks on the catheter and plug can be made by application of ink, laser radiation, etc. The plug, introducer catheter, or portions thereof may be radiopaque. The plugs can be constructed and dimensioned for delivery over other members, e.g. guidewires, fascial dilators.

What is claimed is:

1. A plug for treating an incision through tissue and the wall of a body lumen, comprising:

a sealing member primarily formed of a first healing promoting substance that rapidly expands upon exposure to body fluid, said sealing member having an elongate generally tubular shape and constructed to be introduced axially into the incision and be moveable axially therein, the sealing member including portions constructed to define an integral flow path extending from an opening, disposed near a distal end of the sealing member, to a proximal end of the sealing member, walls of the integral flow path being formed by a second healing promoting substance that expands less rapidly than said first healing-promoting substance, the flow path being accessed from the opening to allow body fluid to flow in contact with the walls formed of said second healing promoting substance and from the opening along the flow path to the proximal portion of the plug when a portion of said plug including said opening is exposed to the interior of said body lumen.

2. The plug of claim 1 wherein said flow path is formed by a lumen that is accessed through said opening near the distal end of said plug.

3. The plug of claim 2 wherein the walls of said lumen are formed of said second healing-promoting substance.

4. The plug of claim 1 wherein a distal end of the sealing member includes an outer coating of a non-hemostatic material.

5. The plug of claim 1 wherein the sealing member includes a series of marks with known axial distance relationships to the most distal portion of flow path that is accessed from the side of said member.

6. The plug of claim 1 wherein the sealing member includes a delivery lumen sized and constructed to allow delivery of said plug into the incision over a catheter.

7. The plug of claim 6 wherein said delivery lumen is sized and constructed to allow sliding delivery of said member over an introducer catheter.

8. A plug for treating an incision through tissue and the wall of a body lumen, comprising:

a sealing member primarily formed of a first healing promoting substance that rapidly expands upon exposure to body fluid, said sealing member having an elongate generally tubular shape and constructed to be introduced axially into the incision and be moveable axially therein, the sealing member including portions constructed to define an integral flow path extending from an opening, disposed near a distal end of the sealing member, to a proximal end of the sealing member, walls of the integral flow path being formed by a second healing promoting substance that expands less rapidly than said first healing-promoting substance, the flow path being accessed from the opening to allow body fluid to flow in contact with the walls formed of said second healing promoting substance and from the opening along the flow path to the proximal portion of the plug when a portion of said plug including said opening is exposed to the interior of said body lumen, wherein said second healing-promoting substance is in the form of a thin coating.

9. The plug of claim 8 wherein said second healing-promoting substance coats substantially the outer exposed portions of said sealing member.

10. The plug of claims 1 or 8 wherein said integral flow path comprises an open flow channel, such that, when said sealing member is in said incision channel said flow path is formed by said flow channel and the tissue on the wall of said incision adjacent said flow channel.

11. The plug of claim 10 wherein said flow channel has an oblong cross section with depth being greater than the width.

12. The plug of claim 11 wherein the depth of said flow channel is at least about one fourth of the overall diameter of said generally tubular member.

13. A system for treating an incision through tissue and the wall of a body lumen, comprising:

a catheter having a proximal portion constructed to remain outside the body and an elongate generally tubular distal portion that is constructed to be introduced axially into said incision, a sealing member formed primarily of a first healing promoting substance that rapidly expands upon exposure to body fluid, said sealing member having an elongate generally tubular shape and constructed to be introduced axially into the incision, the sealing member including portions constructed to define an integral flow path extending from an opening, disposed near a distal end of the sealing member, to a proximal end of the sealing member, walls of the integral flow path being formed by a second healing promoting substance that expands less rapidly than said first healing-promoting substance, said flow path being accessed from the opening to allow body fluid to flow in contact with the walls formed of said second healing promoting substance from the opening along the flow path to the proximal portion of the plug when a portion of said plug including said opening is exposed to the interior of said body lumen, said sealing member being constructed and dimensioned to be guided into said incision by said catheter.

14. The system of claim 13 wherein said catheter includes an inner lumen adapted for introducing a medical device to said body lumen.

15. The system of claim 14 wherein said sealing member is slidably disposed on said catheter.

16. The system of claim 14 wherein said sealing member is constructed to be introduced into said incision simultaneously with said catheter and released from said catheter by sliding said catheter proximally relative to said sealing member.

17. A method of positioning a sealing member within an incision through tissue and the wall of a body lumen, comprising:

providing a sealing member formed primarily of a first healing promoting substance that rapidly expands upon exposure to body fluid, said sealing member having an elongate generally tubular shape and constructed to be introduced axially into the incision and be moveable axially therein, the sealing member including portions constructed to define an integral flow path extending from an opening, disposed near a distal end of the sealing member, to a proximal end of the sealing member, walls of the integral flow path being formed by a second healing promoting substance that expands less rapidly than said first healing-promoting substance, said flow path being accessed from the opening to allow body fluid to flow from the opening into the flow path to the proximal portion of the plug when a portion of said plug including said opening is exposed to the interior of said body lumen, introducing the sealing member within the incision until the access opening is exposed to the interior of the body lumen so that a flow of body fluid is provided to the integral flow path in contact with the walls formed of said second healing promoting substance; and moving the sealing member in an axial direction until the flow of body fluid provided to the integral flow path ceases.

18. The method of claim 17 wherein the introducing step further comprises providing the sealing member over a catheter.

19. The method of claim 18 comprising introducing the catheter into the incision prior to introducing the sealing member.

20. The method of claim 19 comprising introducing the catheter and sealing member into the incision simultaneously.

21. A plug for treating an incision through tissue and the wall of a body lumen, comprising:

a sealing member formed primarily of a first healing promoting substance that rapidly expands upon exposure to body fluid, said sealing member having an elongate generally tubular shape and a longitudinal axis, said sealing member constructed to be introduced axially into the incision and be moveable axially therein, the sealing member including portions constructed to define an integral flow path extending from an opening, disposed along a surface substantially parallel to said axis of the sealing member and near a distal end of the sealing member, to a proximal end of the sealing member, walls of the integral flow path being formed by a second healing promoting substance that expands less rapidly than said first healing-promoting substance, the flow path being accessed from the opening to allow body fluid to flow from the opening along the flow path to the proximal portion of the plug when a portion of said plug including said opening is exposed to the interior of said body lumen.

22. The plug of claim 21 wherein the sealing member further comprises a delivery lumen separate from the integral flow path and sized and constructed to allow delivery of the plug over a introducing device.

23. The plug of claims 21 or 22 further comprising a removable support lumen disposed within the integral flow path.

24. The plug of claim 23 wherein the removable support lumen disposed is a non-biodegradable substance.

\* \* \* \* \*